United States Patent [19]
Murji et al.

[11] Patent Number: 5,242,435
[45] Date of Patent: Sep. 7, 1993

[54] HIGHLY ABSORBENT AND FLEXIBLE CELLULOSIC PULP FLUFF SHEET

[75] Inventors: Zulfikar Murji, Montreal; Henri Brisebois, Lachenaie, both of Canada

[73] Assignee: Johnson & Johnson Inc., Canada

[21] Appl. No.: 637,404

[22] Filed: Jan. 4, 1991

[51] Int. Cl.$^5$ ............................................. A61F 13/15
[52] U.S. Cl. .................................... 604/374; 604/383; 604/385.1; 604/378
[58] Field of Search ............... 604/368, 369, 366, 378, 604/383, 385.1, 381, 382

[56] References Cited

U.S. PATENT DOCUMENTS

| | | | |
|---|---|---|---|
| 3,886,941 | 6/1975 | Duane et al. | 604/368 |
| 4,333,979 | 6/1982 | Sciaraffa et al. | 604/380 |
| 4,596,567 | 6/1986 | Iska | 604/368 |
| 4,960,477 | 10/1990 | Mesek. | |
| 5,069,676 | 12/1991 | Ito et al. | 604/378 |

Primary Examiner—Randall L. Green
Assistant Examiner—R. Clarke

[57] ABSTRACT

A highly absorbent and flexible calendered and perfembossed cellulosic pulp fluff sheet for use in disposable absorbent products such as sanitary napkins, wound dressings, bandages, incontinence pads, disposable diapers and the like. The invention also extends to a method for manufacturing the highly absorbent and flexible pulp fluff sheet and its method of use in disposable absorbent products.

20 Claims, 10 Drawing Sheets

Fig.14 sample
plexiglass plate
support

Fig.16 sample
load cell
stationnary curve
moving curve

HIGHLY ABSORBENT AND FLEXIBLE CELLULOSIC PULP FLUFF SHEET

FIELD OF THE INVENTION

The invention relates to the general field of fluid absorbing products and, more particularly, to a highly absorbent and flexible pulp sheet. More specifically, the flexible and absorbent sheet is a densified and mechanically worked cellulosic pulp fluff material which has a high structural integrity and provides a soft, thin and flexible fluid absorbent core having good wicking characteristics, well-suited for use in disposable absorbent products such as sanitary napkins, wound dressings, bandages, incontinence pads, disposable diapers and the like. The invention also provides a method of preparing such highly absorbent and flexible cellulosic pulp fluff sheet and its method of use in disposable absorbent products.

BACKGROUND OF THE INVENTION

Many disposable absorbent articles use pulp fluff material as the absorbent core. Such cores are generally soft, flexible and absorbent but tend to be bulky and thick and have poor wicking properties. In addition, pulp fluff cores have poor structural stability, prone to collapsing when wet.

An absorbent structure that has poor wicking properties may increase the likelihood of failure of the absorbent product to hold and contain body fluids. Body fluids will be localized to a certain area of a poorly wicking absorbent core, causing saturation in such area whereby excess fluid may overflow through an external surface of the absorbent product. This overflow may contact the user's garment and cause stains or contact the user's body and cause wet discomfort or rash. It is therefore desirable to provide an absorbent core for disposable absorbent articles which can wick away body fluids from the point of contact with the absorbent core and spread it through the absorbent core to more efficiently utilize the entire surface area of the absorbent core. The improved wicking properties of such an absorbent core provide the capacity for fluids to travel by capillary action throughout the surface area of the absorbent core and thus permit the use of thinner cores, since more absorbent surface area can be made available for absorbing body fluids by such wicking action. Thinner absorbent cores may prove to be more comfortable for the user and less unsightly or obvious when worn under clothes.

Absorbent cores with excellent wicking properties comprising peat moss and wood pulp composite materials are described, for example, in U.S. Pat. Nos. 4,170,515; 4,226,237; 4,215,692; 4,507,112; 4,676,871; and 4,473,440. In accordance with the teaching of these patents, an absorbent structure comprising peat moss as a primary absorbent component is formed as a sheet by air or wet laying of fibers and calendering the sheet to obtain a relatively thin, i.e. from about 0.01 to 0.1 inch thick, a relatively dense, i.e. from about 0.2 to 1.0 gram per cubic centimeter (g/cc) structure. Such absorbent peat moss sheets may be processed to increase their flexibility by subjecting the sheets to mechanical tenderizing such as perf-embossing as described in U.S. Pat. No. 4,596,567 or microcorrugating as described in U.S. Pat. No. 4,605,402.

The peat moss sheets thus formed have a large proportion of extremely tiny pores and capillaries which give them the ability to absorb and retain an enormous capacity of fluid. The peat moss pores swell as they absorb fluid, however, this swelling does not cause a loss of capacity for further absorbing fluid. Rather, the swelling contributes to the ability of the sheet to retain fluid while generally maintaining the structural integrity of the absorbent structure in use.

The wicking properties of the above-described peat moss sheets provide the ability for the sheets to be highly absorbent and thin. The flexibility of peat moss sheets may be improved by perf-embossing and/or microcorrugating as described above.

While peat moss sheets make excellent absorbent and wicking cores for disposable absorbent articles, they have limitations. Peat moss sheets may not be readily available particularly in areas which lack the critical raw material, i.e. peat moss or sphagnum moss of desirable age, structure and moisture content. Peat moss sheets also are relatively dark in color and may not be aesthetically acceptable for use in all absorbent products.

Having regard to the foregoing, it is desirable to provide a thin, absorbent and wicking core for disposable absorbent articles which may be substituted for peat moss sheets or pulp fluff sheets.

Attempts to utilize other cellulosic pulp materials such as Kraft wood pulp boards as absorbent cores have not been successful because they tend not to have as much absorbent capacity as peat moss composite sheets but more importantly Kraft wood pulp boards cannot be sufficiently softened for their intended use. While the flexibility and other characteristics of such Kraft wood pulp boards may be improved by perf-embossing and/or microcorrugating techniques, such products still do not provide a desirable combination of absorption capacity and fluid penetration, wicking rates and most importantly a sufficient degree of flexibility for optimal use in disposable absorbent products, particularly sanitary napkins.

OBJECTS AND STATEMENT OF THE INVENTION

It is, therefore, an object of the present invention to provide a cellulosic pulp fluff sheet which does not utilize peat moss in its structure but has sufficient absorption capacity, good wicking characteristics as well as a relatively short fluid penetration time, and possessing good flexibility for use in disposable absorbent articles. Optimal flexibility of such products requires that the product be comfortably soft and flexible to the wearer but stiff and strong enough to withstand bunching and breakage when subjected to mechanical stress in a dry and a wet state.

Another object of the invention is a method for manufacturing such a cellulosic pulp fluff sheet.

Yet, another object of the invention is to provide a disposable absorbent product which uses such a cellulosic pulp fluff sheet as an absorbent core.

The present inventors have discovered that when conventional cellulosic pulp fluff material is densified by mechanical compression, such as calendering, and subsequently embossed, a highly absorbent and flexible sheet is obtained, having exceptionally good wicking characteristics. The improvement in the wicking properties is a direct result of the embossing process which selectively compacts the densified cellulosic pulp fluff material imparting a fiber density profile of alternating high and low fiber density zones. (For the purpose of this specification, the term "high fiber density zones" and "low fiber density zones" should be construed in a relative manner indicating that one zone has a higher fiber density than the other, without reference to the absolute density values of the zones). The high fiber density zones have the ability to disperse fluid throughout the entire surface of the absorbent sheet by virtue of excellent wicking properties, establishing a network of capillary-action channels interconnecting the low fiber density zones which have the task of permanently absorbing and retaining the fluid. When a fluid mass is released on a certain point of the absorbent sheet, the fluid will rapidly penetrate the low fiber density zones immediately underneath the fluid impact point. Local overflow is avoided by the wicking power of the high fiber density zones which transfer fluid from saturated to nonsaturated low fiber density zones, thus spreading the fluid throughout a larger absorbent volume.

In addition to the above, the embossing process also increases the flexibility of the densified pulp fluff material. The selective compaction creates hinges permitting the absorbent sheet to become more pliable and compliant.

The densification step of the cellulosic pulp fluff material, prior to the embossing stage, is an important aspect of the invention because it increases the cohesion of the fibrous web, with a resultant increase in structural stability. With regard to the fluid absorption characteristics, the densification has the effect of increasing the capability of the fibrous material to prevent absorbed fluid to escape. In contrast, untreated pulp fluff does not have the ability to lock in and retain absorbed fluid due to the large voids present in the fibrous network and a leak-through failure can occur. When fluid is discharged on the densified and embossed cellulosic pulp fluff sheet, the fluid mass is absorbed in low fiber density zones which, by virtue of the improvement in the fluid retention characteristics, can hold the fluid for a sufficiently long period of time to allow the fluid to be pulled throughout the absorbent sheet by the wicking high fiber density zones.

Objectively, the densification will increase to some degree the fluid penetration time over untreated pulp fluff, however, on balance an overall gain in efficiency is observed due to the improvement in fluid retention and structural stability.

While it is known in the art of manufacturing absorbent products to process peat moss by calendering and embossing, the objective of such treatment is solely to selectively crush the peat moss structure to improve its comfort factor. In contrast, the inventors have found that when this process is applied to pulp fluff, surprisingly, a considerable improvement in the fluid absorption characteristics is obtained, doubled by an increase in the structural stability of the pulp fluff material.

In a preferred embodiment, the desired fiber density profile of the densified cellulosic pulp fluff sheet is obtained by a perf-embossing process which has the advantage over embossing alone, to selectively perforate the pulp fluff sheet, opening-up its structure for an increase in flexibility and also creating vertical channels enhancing fluid absorption in the Z axis.

Accordingly, the invention provides a cellulosic pulp fluff absorbent sheet which has the combined desirable advantages of rapid fluid penetration, high absorption capacity, excellent wickability characteristics such that fluid is transported via capillary action throughout the surface area to make efficient use of the available fluid absorption surface of the sheet, also possessing good drying power and an excellent structural stability.

The densified and embossed cellulosic pulp fluff sheet according to the invention is well-suited as an absorbent core for disposable absorbent products such as sanitary napkins, wound dressings, bandages, incontinence pads, disposable diapers and the like. When incorporated in a sanitary napkin for example, it is sufficiently flexible to be worn comfortably and at the same time, it has a sufficient structural integrity to prevent bunching and breakage when subjected to mechanical stress in the dry or in the wet state.

In preferred embodiments of the invention, the dry thickness of the densified and embossed cellulosic pulp fluff sheet is in the range of about 0.075 to 0.20 inches measured at 0.05 pounds per square inch (psi) pressure, preferably in the range of about 0.09 to 0.15 inches at 0.05 psi pressure. The dry tensile strength of the densified and embossed cellulosic pulp fluff sheet is at least of about 1 pound per inch (lbs/inch) in the machine direction and more preferably at least of about 2 lbs/in. in the machine direction. The density of the densified and embossed cellulosic pulp fluff sheet is in the range of about 0.1 to 0.3 grams per cubic centimeter (g/cc) and more preferably of about 0.2 to 0.25 g/cc, and its absorbent capacity is at least of about 4 cubic centimeters per gram (cc/g) and more preferably of about 6 cc/g.

The preferred cellulosic pulp fluff starting material utilized in accordance with the invention is a sulfate, sulfite or Kraft wood pulp, but other cellylosic pulps may be used, such as, for example, debonded pulp, unbleached wood pulp or wood pulp bleached by chlorine processes or hydrogen peroxide, and chemical thermal mechanical pulp.

As embodied and broadly described herein, the invention further comprises a disposable absorbent product having an absorbent core with good wicking and absorption characteristics comprising the flexible absorbent densified and embossed cellulosic pulp fluff sheet which is sufficiently pliable and compliant to be comfortably worn by the wearer of the disposable absorbent product. In preferred embodiments of the invention, the disposable absorbent product is selected from the group consisting of sanitary napkins, incontinence products, diapers, and wound dressings. In a more preferred embodiment of the invention, a thin, absorbent and flexible sanitary napkin is provided which has an improved absorbent core comprising a calendered and a perf-embossed cellulosic pulp fluff sheet. In a most preferred embodiment of the invention the absorbent core is of optimal flexibility to be comfortable to the product wearer but stiff enough to substantially retain its original shape in use or after wetting.

As embodied and broadly described herein, the invention further comprises a method of preparing a highly absorbent and flexible cellulosic pulp fluff sheet, comprising the steps of:

a) forming a densified pulp fluff sheet by mechanically compressing cellulosic pulp fluff material; and b) embossing the densified pulp fluff sheet of step (a) to impart the densified pulp fluff sheet with a fiber density profile exhibiting alternating high and low fiber density zones, while impressing a multitude of hinge areas for reducing the stiffness of the pulp fluff sheet.

In a preferred embodiment, the density of the mechanically compressed cellulosic pulp fluff sheet of step (a) has a density in the range of about 0.25 to 0.55 g/cc and more preferably in the range of about 0.35 to 0.50 g/cc, and a dry thickness in the range of about 0.03 to 0.07 inches measured at 0.05 psi pressure and more preferably of about 0.04 to 0.06 inches measured at 0.05 psi pressure.

As embodied and broadly described herein, the invention further comprises a method of providing good fluid absorption in a thin and comfortable sanitary napkin comprising the step of incorporating as an absorbent core in the sanitary napkin, a densified and embossed cellulosic pulp fluff sheet. In a preferred embodiment, the absorbent core has a dry thickness in the range of about 0.075 to 0.2 inches measured at 0.05 psi pressure, and more preferably in the range of about 0.09 to 0.15 inches at 0.05 psi pressure, an absorbent capacity approximately of at least 4 cc/g, more preferably of at about 6 cc/g, a density in the range of about 0.1 to 0.3 g/cc and more preferably in the range of about 0.2 to 0.25 g/cc, a lateral flexibility in the dry state in the range of about 700 to 1700 grams (g) and preferably in the range of about 1100 to 1400 g, a lateral flexibility in the wet state in the range of about 550 to 950 g, and a dry tensive strength in the machine direction of at least about 1 lb/inch and more preferably of at least about 2 lbs/inch.

DESCRIPTION OF PREFERRED EMBODIMENTS

Reference will now be made in detail to preferred embodiments of the invention, examples of which are illustrated in the following example sections.

To achieve the object of the invention of providing a highly absorbent, flexible and good wicking core for disposable absorbent products which may be an economical and suitable replacement for peat moss composite sheets or unprocessed cellulosic pulp fluff sheets, the present inventors have made the unexpected discovery that cellulosic pulp fluff material, particularly wood pulp fluff, which when densified by mechanical compression, such as calendering for example, and subsequently embossed, by perf-embossing for example, to impart a pattern of alternating high fiber density and low fiber density zones, will provide a flexible, highly absorbent and wicking core possessing a high structural integrity.

Figure 1:
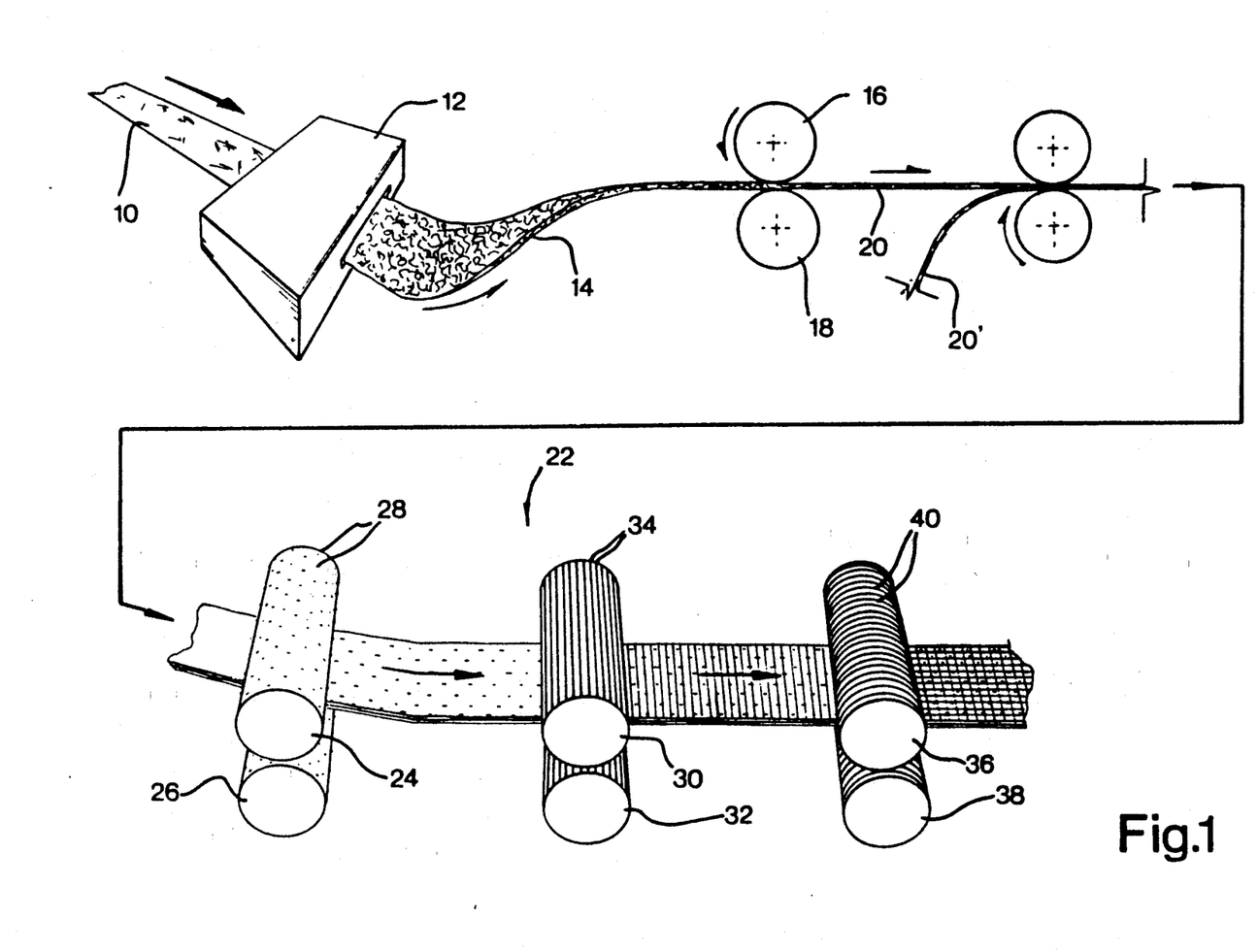
FIG. 1 is a graphic illustration of the process for manufacturing the densified and perf-embossed cellulosic pulp fluff sheet according to the invention.

FIG. 1 graphically depicts a highly preferred embodiment of the method for providing the highly absorbent and flexible densified and embossed cellulosic pulp fluff sheet according to the invention. A commercially available pulp board 10 in a continuous sheet form is subjected to mechanical defiberization and maceration in a grinding mill 12 to produce a pulp fluff web 14. This step is not an essential aspect of the invention because the method of producing pulp fluff material is well-known in the art of constructing fluid absorbent structures. In addition, pulp fluff being a commercially available product itself, the on-site production of the pulp fluff web is not a necessity.

The pulp fluff web 14 is subjected to a two-stage calendering process to uniformly compress and densify the web creating a network of randomly oriented fibers which has a superior resistance, preventing loss of integrity under the effect of mechanical stress applied during subsequent treatments, and providing a good structural stability to the finished product. In addition, the densification also enhances the ability of the fibrous web to retain fluid within the fibrous network, due to a reduction of inter-fiber distances, as it will be discussed hereinafter.

The first stage of the calendering station includes a pair of compression rolls 16 and 18 forming a nip through which the pulp fluff web 14 is passed. The calendering pressure at the first stage is not critical because the primary objective is to stabilize the web thickness, not to impart a precise density to the web. Accordingly, a wide range of pressures are possible without significantly affecting the properties of the final product. For practical purposes, a relatively low pressure in the order of 10 to 50 pounds per linear inch (pli) is used because inexpensive small capacity calendering equipment is adequate to perform this operation.

The slightly densified pulp fluff web 20 obtained at the first stage of the calendering process is subjected to a second stage mechanical compression achieved by a setup essentially identical to that used at the first stage, except the calendering pressure is much higher, approximately in the range of about 200 to 1300 pli, preferably in the range of about 300 to 800 pli, and most preferably in the range of about 400–500 pli, and the thickness of the pulp fluff web 20 passing through the second stage nip is doubled to achieve a higher basis weight product. A double layer web is achieved by feeding simultaneously with the pulp fluff web 20 a web 20' having identical characteristics.

By using a multi-stage calendering station and by increasing, between the stages, the thickness of the processed pulp fluff web a relatively high basis weight material can be obtained without the necessity of providing a large capacity calendering station operating at high pressures. Although it may be envisaged to use a single stage calendering station, in addition to the high calendering pressure required, the basis weight of the pulp fluff web 14 must also be increased which may present some handling problems because the web becomes bulky.

The double layer compressed pulp fluff web leaving the calendering station is fed to a perf-embossing station designated comprehensively by the reference numeral 22. The perf-embossing technique first perforates the densified pulp fluff web, then sequentially embosses the resulting material in the Y (cross-direction) and X (machine direction).

The "PERF" operation (first step), best illustrated in FIGS. 2, 3, 4 and 5, is performed by passing the web between a pair of rolls 24 and 26 provided with intermeshing and non-contacting teeth 28 perforating the web by shearing action mainly to open the structure of the cellulosic material to reduce its stiffness, while densifying other regions of the web.

Figure 3:
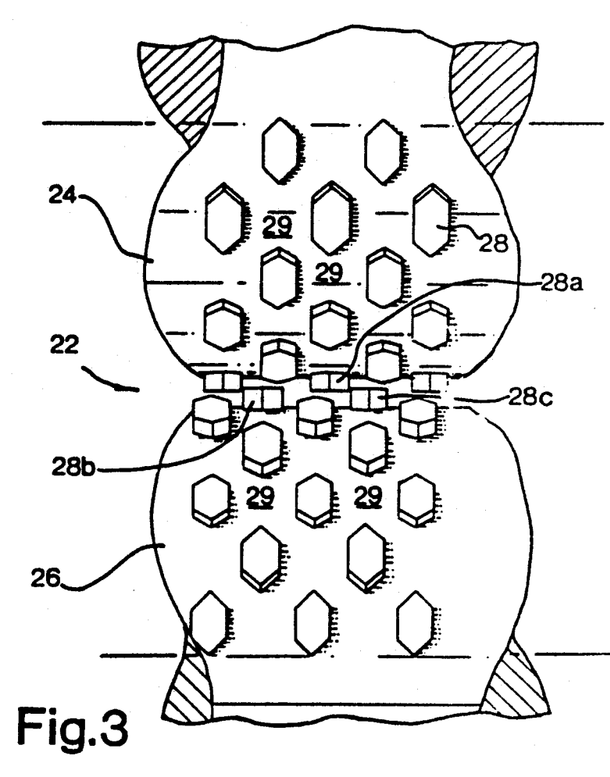
FIG. 3 is a fragmentary front elevational view of the perforation rolls shown in FIG. 2, the web of densified cellylosic pulp fluff to be treated being omitted for illustrating the interrelation between the perforation teeth on the rolls.
Figure 4:
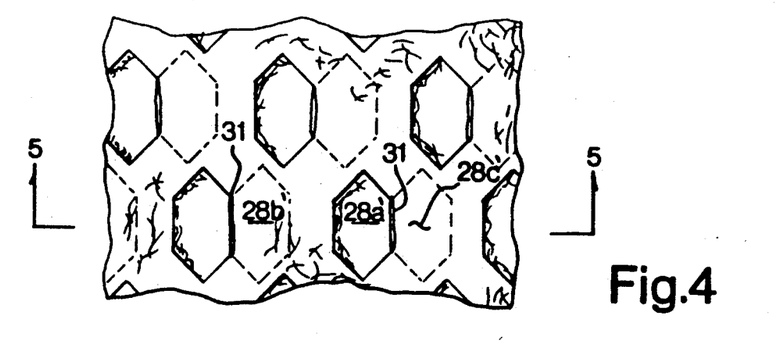
FIG. 4 is an enlarged top view of the densified cellylosic pulp fluff web treated by the perforation rolls shown in FIGS. 2 and 3, illustrating the web topography resulting from the interaction of the perforation teeth.
Figure 5:
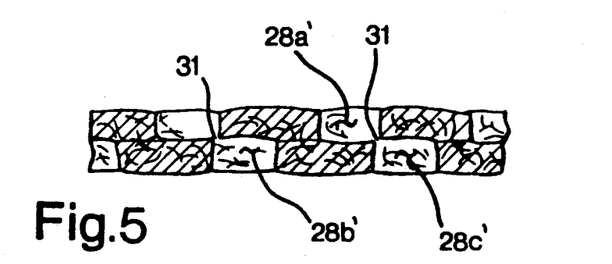
FIG. 5 is a sectional view taken along lines 5—5 in FIG. 4.

FIGS. 3, 4 and 5 illustrate well the selective treatment of the pulp fluff web as a result of the interaction between the teeth 28. The teeth 28 on the companion rolls 24,26 are so arranged that tooth 28a on top roll 24 is off-center the inter-teeth void defined between adjacent and axially aligned teeth 28b and 28c. The shearing action actually occurs between teeth 28a,28c during intermeshing, locally perforating the fibrous web 20.

The rolls 24 and 26 in addition to shearing locally the web 20, also somewhat compress and further densify the pulp fluff material. Such compression occurs between the flat top surface of each tooth 28 and the smooth arcuate surface 29 of the opposite roll facing the tooth during intermeshing. In practice, such selective compression does not significantly alter the characteristics of the final product. If it desired to avoid it completely, it suffices to increase the teeth height, allowing to increase the gap between rolls 24,26 without affecting the shearing action.

The above can be better visualized by examining the structure of the pulp fluff web after treatment by the perforation rolls 24 and 26. The imprints of teeth 28 are identified by the same numerals used to designate the teeth, followed by "'". The imprints 28a' and 28c' are separated by a slit 31 extending entirely throughout the pulp fluff web resulting from the shearing action of the teeth 28a and 28c.

Figure 2:
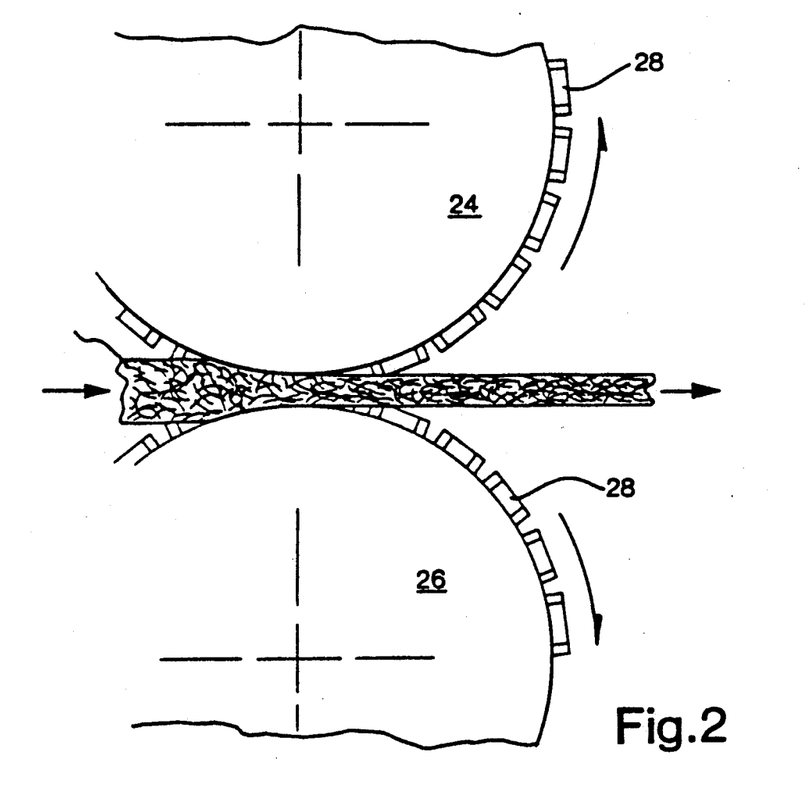
FIG. 2 is a vertical cross-sectional view of the perforation rolls which constitute the first stage of the perf-embossing treatment.

In a preferred embodiment, interference i.e. overlap between the teeth 28 of the perforating rolls 24 and 26 is set at approximately 35 thousandths of an inch (mils). This setting may vary according to the web thickness, humidity and other factors.

Figure 6:
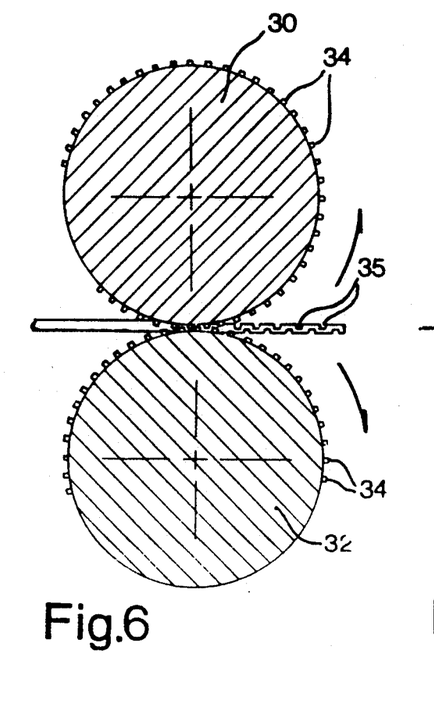
FIG. 6 is a vertical cross-sectional view of the cross-direction embossing rolls which constitute the second stage of the perf-embossing treatment.
Figure 7:
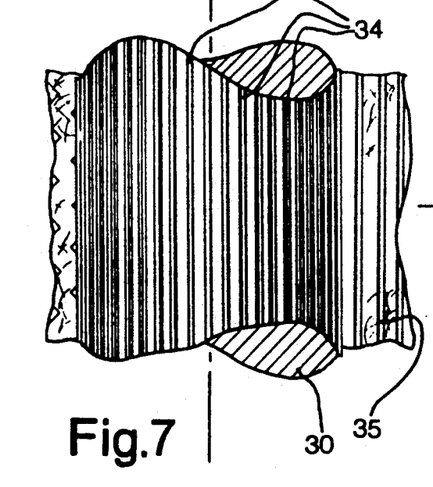
FIG. 7 is a top view of one of the cross-direction embossing roll, also showing the resulting embossing pattern created on the cellylosic pulp fluff web.

The second step of the perf-embossing operation consists of embossing the perforated pulp fluff web in the cross-direction by passing the pulp fluff web between a pair of rolls 30,32 with intermeshing longitudinally extending flutes 34. FIGS. 6 and 7 best illustrate the cross-direction embossing rolls 30 and 32 and the tridimensional structure imparted to the pulp fluff web. The flutes 34 imprint lines 35 on each surface of the pulp fluff web by locally compacting the fibrous material under the effect of mechanical compression.

It will be appreciated that the cross-direction embossing rolls alter the structure of the pulp fluff web in two significant aspects. Firstly, the lines 35 form miniature hinges extending transversely to the pulp fluff web increasing its flexibility in the longitudinal direction. Secondly, the fiber density in the vicinity of the lines 35 is increased by virtue of the mechanical compaction necessary to form the impressions. As a result, a distinct fiber density profile is imparted to the pulp fluff web, consisting of high and low fiber density zones alternating in the machine direction. A desirable consequence of the achieved variable fiber density, as it will be discussed in more detail hereinafter, is a selective alteration of the fluid absorption characteristics of the pulp fluff web, creating spaced apart high density, relatively non-absorbent areas, providing a fluid wicking action in a transverse direction to the pulp fluff web.

In a preferred embodiment, the interference, i.e. overlap between flutes 34 of the rolls 30,32 is set at approximately 5 mils. This setting may vary according to the specific operating conditions.

Figure 8:
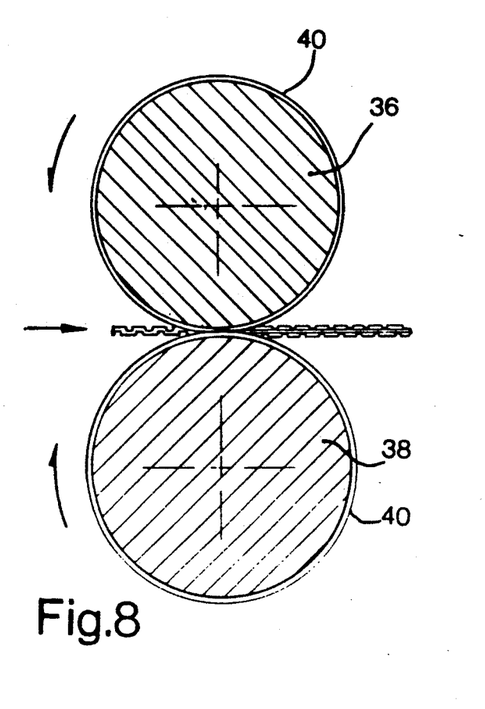
FIG. 8 is a vertical cross-sectional view of the machine-direction embossing rolls which constitute the third and last stage of the perf-embossing treatment.
Figure 9:
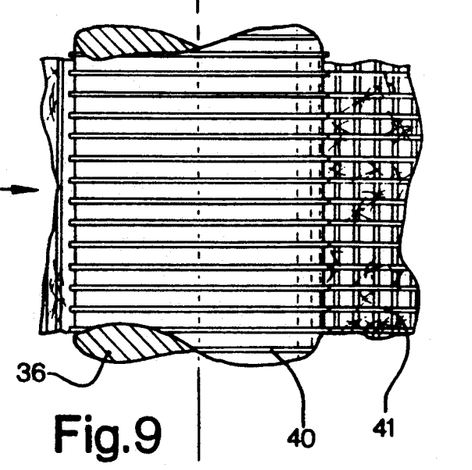
FIG. 9 is a top view of one of the machine-direction embossing rolls, also showing the resulting embossing pattern created on the cellulosic pulp fluff web.

The last step of the perf-embossing operation consists in embossing the resultant material in the machine direction by passing the web between parallel rolls 36, 38 having circumferentially extending and intermeshing flutes 40, as best shown in FIGS. 8 and 9. This means a perpendicular impact to the second step operation, creating longitudinal lines 41 to now impart a fiber density profile of alternating high and low fiber density areas in a transverse direction of the pulp fluff web as well as providing longitudinal hinge lines.

In a preferred embodiment, the interference between the machine direction embossing rolls 36,38 is set at 5 mils. This setting may vary according to the specific operating conditions.

The perf-embossing process increases the dimension of the pulp fluff web in the cross-direction by about 5 to 7%.

Figure 10:
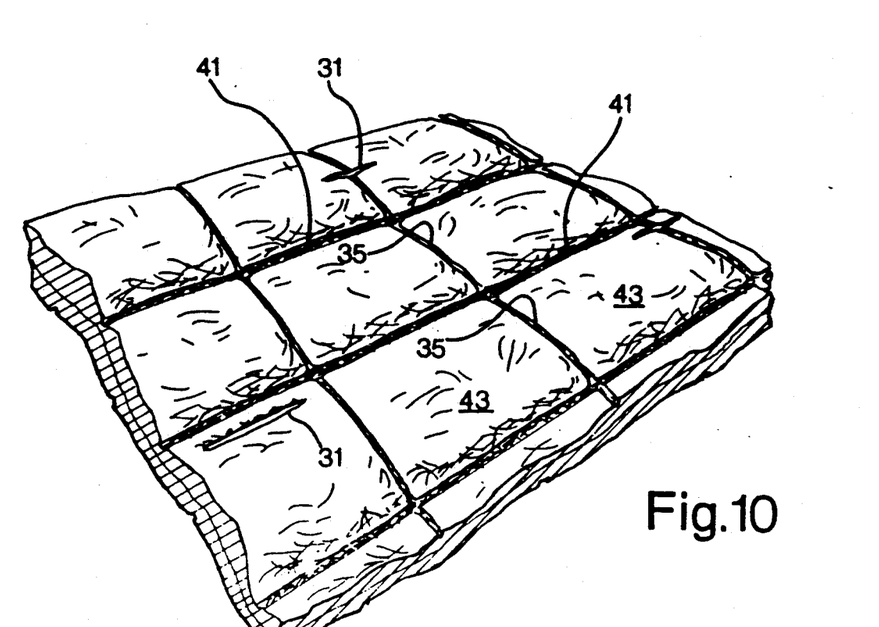
FIG. 10 is an enlarged perspective view of the cellulosic pulp fluff sheet structure resulting from the perf-embossing treatment.

The final structure of the cellulosic pulp fluff sheet, after being calendered and perf-embossed, is shown in FIG. 10. The entire surface of the pulp fluff sheet exhibits a pattern of square low fiber density zones 43 which are separated from one another by longitudinal and transverse lines 41 and 35 respectively. Slits 31 created at the first stage of the perf-embossing treatment are uniformly dispersed throughout the pulp fluff sheet.

From the stand point of fluid absorbency, this structure is particularly advantageous because it combines desirable characteristics, such as superior wicking power, high absorbency and a rapid fluid absorption rate. Fluid discharged on the pulp fluff sheet will penetrate the low fiber density zones 43 immediately underneath the fluid impact point, possibly causing local saturation. However, leak-through failure of the absorbent structure is unlikely to occur by virtue of an improved tolerance to local saturation resulting from the densification of the fibrous network by the calendering process. The densification provides a superior fluid retaining ability, whereby absorbed fluid is captured and held during a sufficient period of time to allow the high fiber density zones to pull and disperse the fluid within the cellulosic pulp fluff sheet by capillary action. In similar conditions, pulp fluff material which has been embossed without being previously densified may not work as well because the low fiber density zones have a limited ability to lock in and retain absorbed fluid and a leak-through failure may occur before the fluid has been dispersed by wicking action.

Fluid penetration within the pulp fluff sheet is enhanced by the slits 31, forming channels in the Z axis of the sheet promoting a faster fluid absorption.

The perf-embossing treatment also contributes to provide desirable mechanical properties to the cellulosic pulp fluff sheet, such as an increased flexibility enhancing the comfort potential of the product. The slits 31 contribute to open-up the fibrous structure at precise locations, thus locally disrupting fiber bonds to render the material more pliable. The lines 35 and 41 constitute miniature hinges, extending throughout the entire surface of the cellulosic pulp fluff sheet to render the material compliant in a transverse and in a longitudinal direction.

The increased flexibility of the cellulosic pulp fluff material achieved by the perf-embossing process is important to provide an absorbent core in a sanitary napkin for example, which is comfortable to the wearer and can conform to various body shapes and movements in use. The optimal flexibility achieved in accordance with the invention provides an absorbent sheet that is flexible enough to meet the comfort criteria but stiff enough to resist product bunching and deforming in use and/or upon wetting. Such optimal flexibility and strength contributes to provide better fit for improved protection against overflow leakages and retention of product shape through use or wetting.

Another surprising advantage of the calendered and perf-embossed cellulosic pulp fluff material over unprocessed cellulosic pulp fluff and tenderized peat moss sheet is the integrity and high tensile strength of the improved pulp fluff core and its resistance to deterioration through wetting and use. Absorbent cores produced in accordance with the present invention preferably have a dry tensile strength in the range from about 1 to about 3 lbs/inch in the machine direction. Further, the absorbent material according to the invention has the combined desirable advantages of better fluid penetration rate than tenderized peat moss and tenderized debonded pulp, high absorption capacity, better wickability characteristics and drying power than unprocessed pulp fluff and tenderized debonded pulp.

The outstanding combination of absorption, flexibility and wicking characteristics of the absorbent core of the invention provides sanitary napkins capable of absorbing menstrual or other body fluids quickly and efficiently and retaining fluid in the absorbent structure of the napkin so as to limit failure. Sanitary napkins utilizing absorbent cores of the invention are flexible and comfortable, yet resistant to bunching, twisting, and deterioration through active use. The absorbent core of the invention can be utilized as an insert or as an entire surface bilayer of a sanitary napkin. For example, the absorbent core of the invention can be utilized as a reservoir layer or insert in conjunction with a cover and transfer layer or because of its short fluid penetration time, it may be used adjacent only a cover layer whereby the absorbent core of the invention serves the dual function of a transfer layer and reservoir layer.

In addition to sanitary napkins, the densified and embossed cellulosic pulp fluff sheet according to the invention may also be used in other absorbent products such as diapers, incontinence products, wound dressings, bandages and also as packaging material to provide dry shipment of goods which may exude moisture in shipment or storage.

The densified and embossed cellulosic pulp fluff material of the invention may be treated with softening agents, such as glycerin or lanolin or others. In addition to softening agents, other absorbent materials such as fibers or "superabsorbent" polymers may be incorporated into the matrix spaces of the absorbent core structure. Such fibers and polymers are described, for example, in U.S. Pat. No. 4,559,050. Further, superabsorbent laminates may be provided in combination with the calendered and perf-embossed cellulosic pulp fluff material to provide extra absorption capacity such as, for example, in incontinence products.

EXAMPLES

The invention will now be illustrated by examples. The examples are not intended to be limiting of the scope of the present invention but read in conjunction with a detailed and general description above provide a further understanding of the present invention and an outline of a process for preparing a sanitary napkin which comprises a calendered and perf-embossed cellulosic pulp sheet as its absorbent core.

The description of the various test procedures to which the materials of Examples 1 and 2 have been subjected, are described in the section entitled "TEST PROCEDURES" following Table 4.

EXAMPLES 1-2

Preparation of Absorbent and Flexible Calendered and Perf-Embossed Cellulosic Pulp Fluff Sheet Wood pulp board, the starting material of the process described in connection with FIG. 1, is available commercially from, for example:

| | |
|---|---|
| Example 1 | Rayfloc (Trademark) produced by ITT Rayonier |
| Example 2 | Supersoft (Trademark) produced by The International Paper Company |

Technical characteristics of these wood pulp boards are provided in Table I.

TABLE I

| | Wood Pulp Board | |
|---|---|---|
| | Ex. 1 | Ex. 2 |
| a) Physical Properties | | |
| Basis weight grams per meter squared (g/m$^2$) | 685 | 690 |
| Density grams per cubic centimer (g/cc) | .525 | .535 |
| b) Structural Integrity | | |
| Dry tensile strength pounds per inch (lbs/inch) | 70 | 95 |
| c) Fluid Absorption | | |
| Penetration time seconds (s) | above 800 | above 3000 |
| 45° Impact capacity | 7.5 | 3.3 |

TABLE I-continued

| Wood Pulp Board | | |
|---|---|---|
| | Ex. 1 | Ex. 2 |
| grams (g) | | |

The boards of Examples 1-2 are mechanically grinded to obtain wood pulp fluff webs, having the characteristics described in Table 2.

TABLE 2

Figure 17:
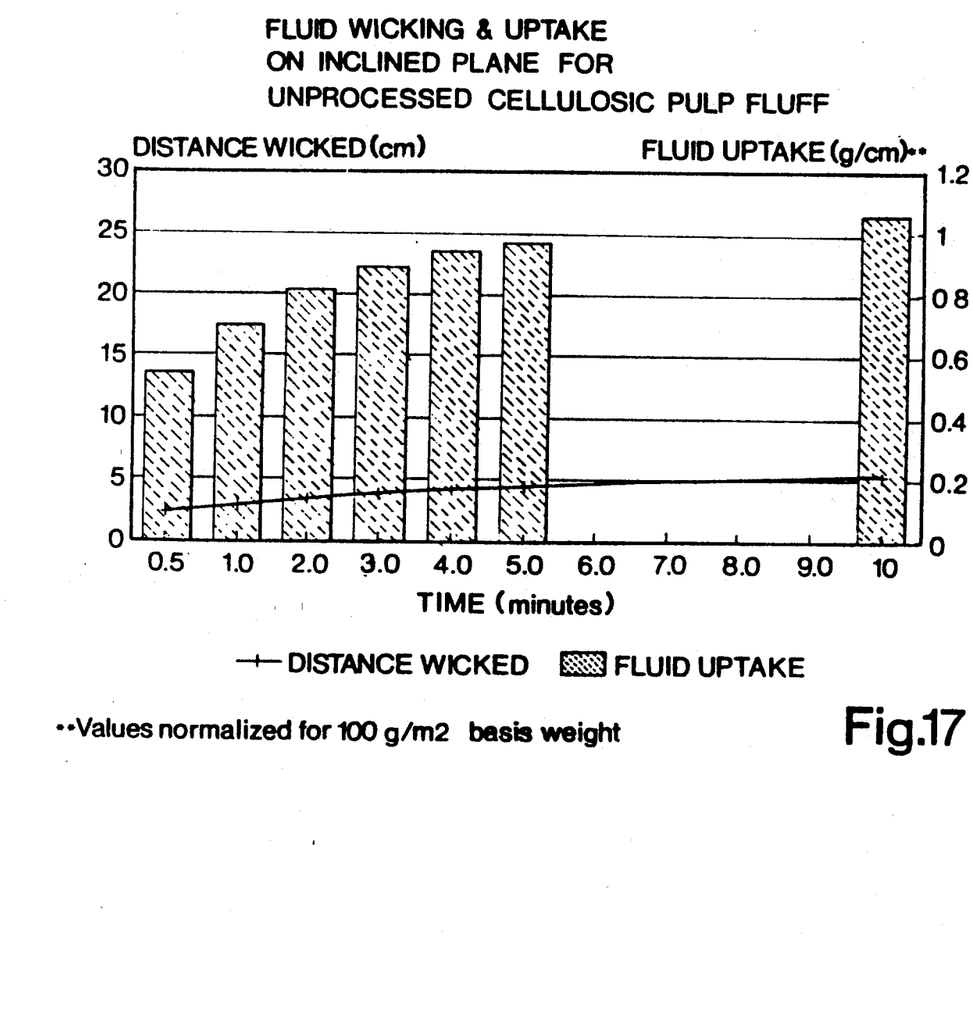
FIG. 17 is a graph of fluid wicking and uptake versus time for unprocessed cellulosic pulp fluff.

| Untreated wood pulp fluff web | | |
|---|---|---|
| | Ex. 1 | Ex. 2 |
| a) Physical Properties | | |
| Basis weight grams per meter squared (g/m$^2$) | 350 | 360 |
| Density grams per cubic centimer (g/cc) | .045 | .045 |
| b) Structural Integrity | | |
| Dry tensile strength pounds per inch (lbs/inch) | virtually nil | |
| c) Fluid Absorption | | |
| Penetration time seconds (s) | 5 | 5 |
| 45° Impact capacity grams (g) | 27 | 27 |
| Capacity cubic centimeters per gram (cc/g) | 14 | 15 |
| Collapse strength* percentage (%) | −24 | −27 |
| Wet-back grams (g) | .51 | .48 |
| Wicking (uptake) | refer to graph FIG. 17 | |
| d) Flexibility | | |
| Lateral compression grams (g) | | |
| i) dry | about 100 | |
| ii) wet | about 100 | |

*negative values indicate collapse

The wood pulp fluff webs of Examples 1-2 are mechanically compressed by the calendering process described in connection with FIG. 1. The double layer calendered webs of Examples 1-2 have the characteristics as described in Table 3.

TABLE 3

| Calendered double layer wood pulp fluff web | | |
|---|---|---|
| | Ex. 1 | Ex. 2 |
| a) Physical Properties | | |
| Basis weight grams per meter squared (g/m$^2$) | 645 | 625 |
| Density grams per cubic centimer (g/cc) | .48 | .42 |
| b) Structural Integrity | | |
| Dry tensile strength pounds per inch (lbs/inch) | 34 | 19 |
| c) Fluid Absorption | | |
| Penetration time seconds (s) | above 800 | above 600 |
| 45° Impact capacity grams (g) | 14.2 | 14.6 |

The calendered webs prepared in accordance with the procedures set out above for Examples 1-2 are treated by perf-embossing as described in this specification. The resulting perf-embossed cellulosic pulp fluff sheets have the characteristics as described in table 4.

TABLE 4

Figure 18:
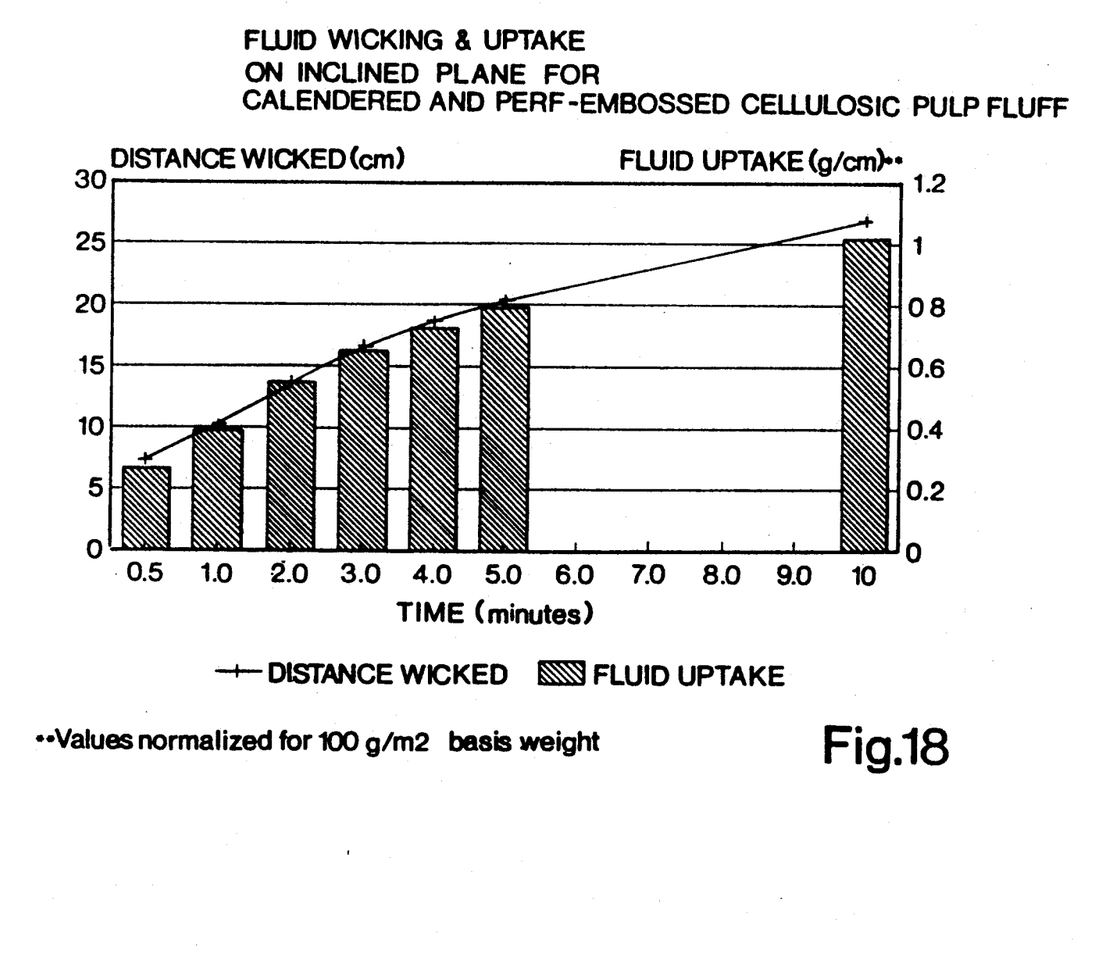
FIG. 18 is a graph of fluid wicking and uptake versus time for calendered and perf-embossed cellulosic pulp fluff according to the invention.

| Calendered and Perf-Embossed Double Layer Wood Pulp Fluff Sheet | | |
|---|---|---|
| | Ex. 1 | Ex. 2 |
| a) Physical Properties | | |
| Basis weight grams per meter squared (g/m$^2$) | 615 | 620 |
| Density grams per cubic centimer (g/cc) | .23 | .21 |
| b) Structural Integrity | | |
| Dry tensile strength pounds per inch (lbs/inch) | 2.5 | 1.1 |
| c) Fluid Absorption | | |
| Penetration time Seconds (s) | | |
| i) rigid sample support | 64 | 62 |
| ii) resilient sample support | 29 | 34 |
| 45° Impact capacity grams (g) | 21.5 | 23.1 |
| Capacity cubic centimeters per gram (cc/g) | 5.8 | 6.6 |
| Collapse strength* percentage (%) | +46 | +49 |
| Wet-back grams (g) | .15 | .16 |
| Wicking (uptake) | refer to graph FIG. 18 | |
| d) Flexibility | | |
| Lateral compression grams (g) | | |
| i) dry | from 700 to 1700 | |
| ii) wet | from 550 to 950 | |

*positive values indicate swelling.

DESCRIPTION OF TEST PROCEDURES

A) BASIS WEIGHT

Purpose: To determine the basis weight of the absorbent material.

Test procedure: One square foot sample is weighted and the basis weight is calculated in grams per meter squared (g/m$^2$).

B) THICKNESS

Purpose: To determine the thickness of the absorbent material.

Test procedure: 
1) Wood Pulp Board: The thickness of the board material is measured with a TMI thickness gauge at 7 psi pressure with a 5/8 inch diameter foot (TAPPI standard T411 0S-76);
2) Fluffed, Calendered, Perf-Embossed Wood Pulp: The thickness of the sample is measured at 0.05 psi pressure with a compressometer using a 2 inch diameter foot (ASTM D-1777).

C) DENSITY

Purpose: To determine the density of an absorbent material under a predetermined pressure.

Test procedure:
1) Wood Pulp Board: The density is obtained by measuring the weight of a 1 square foot sample and dividing it by its volume (thickness × area of sample);
2) Fluffed, Calendered, Perf-Embossed Wood Pulp: The density of the processed material is obtained by taking the weight of a 2 inch × 3 inch sample and dividing it by its volume (thickness × area of sample).

D) TENSILE STRENGTH

Purpose: To determine the structural strength of the absorbent material by measuring the force required to rupture the sample.

Test procedure: The tensile strength is measured by recording the force required to rupture a 1 inch wide sample placed between two jaws 3 inches apart and

Figure 12:
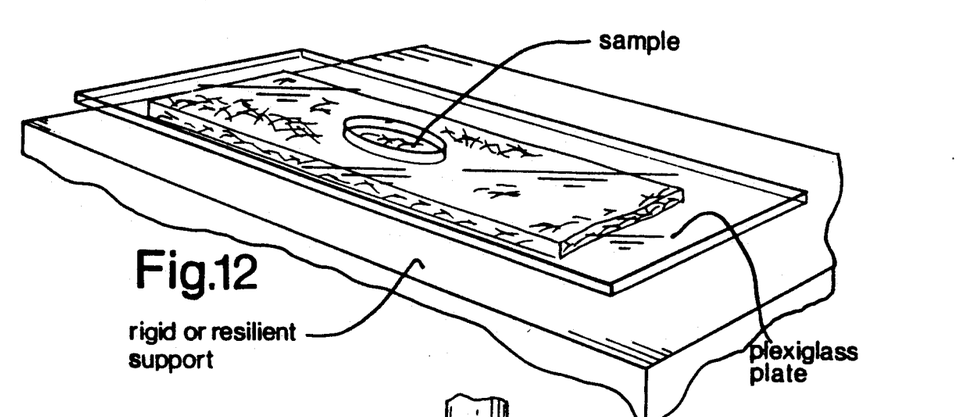
FIG. 12 is a perspective view of a set-up for conducting a fluid penetration time test procedure.
Figure 13:
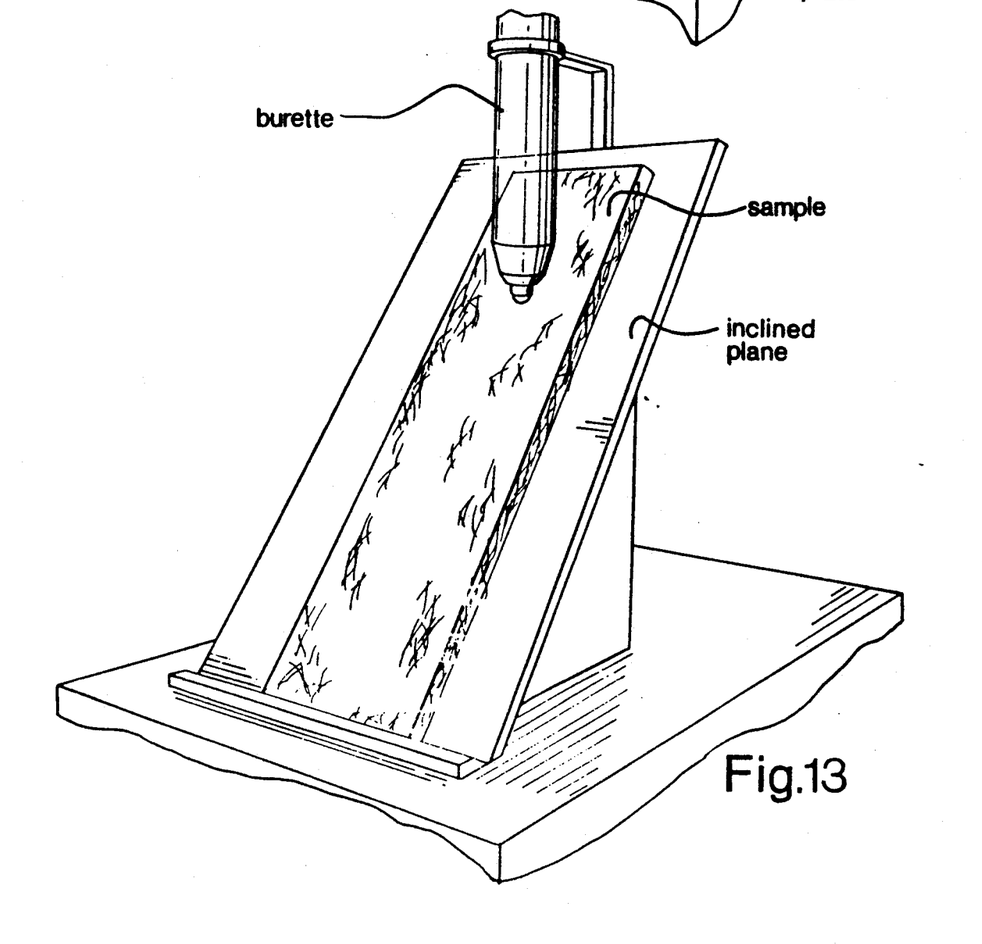
FIG. 13 is a perspective view of a set-up for conducting a 45° impact capacity test procedure.
Figure 14:
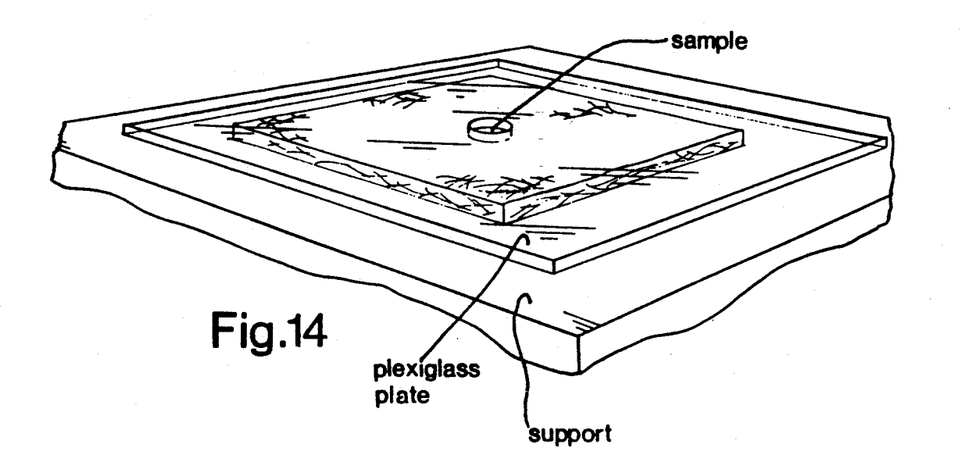
FIG. 14 is a perspective view of a set-up for conducting a fluid capacity and collapse test procedure.
Figure 15:
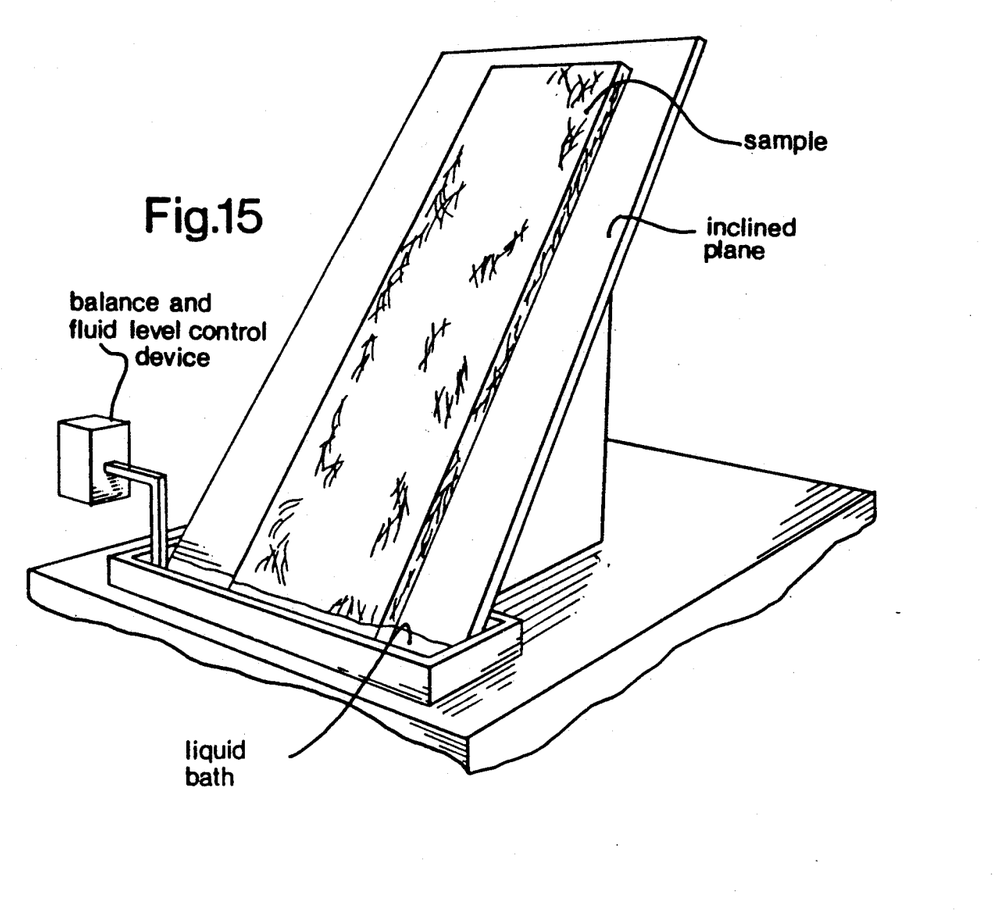
FIG. 15 is a perspective view of an apparatus for conducting an inclined plane wicking test procedure.
Figure 16:
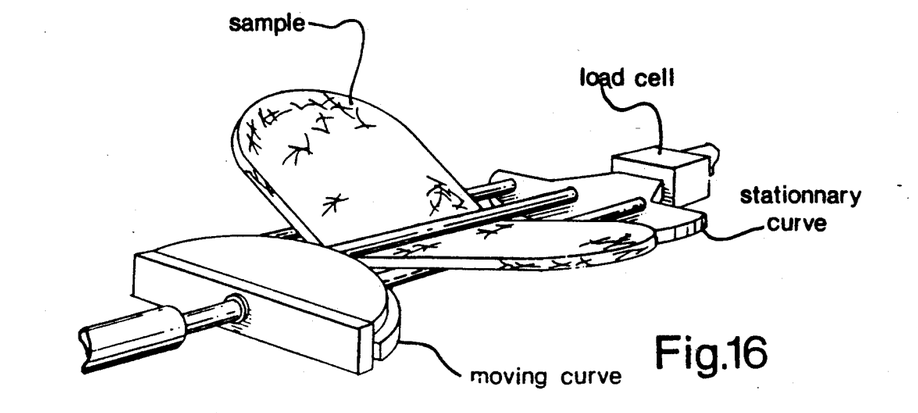
FIG. 16 is a perspective view of an apparatus for conducting a lateral stability/flexibility test procedure.

| | DESCRIPTION OF TEST PROCEDURES |
|---|---|
| E) PENETRATION TIME | |
| Purpose: | To determine the penetration time of an absorbent material by measuring the time required to completely absorb a finite amount of fluid. |
| Test procedure: | The time required for a 2 inch × 8 inch sample under 0.04 psi pressure covered by a plexiglass plate, as shown in FIG. 12, to absorb 5 cubic centimeters of test fluid fed to the sample through an oval orifice on the plate measuring 1½ inches × ⅜ of an inch. The sample may be supported on either a rigid or a resilient base. The latter embodiment is useful for absorbent materials which swell when absorbing fluid because the resilient cushion can yield allowing for further expansion. The penetration time is recorded when all free liquid had disappeared from the surface of the sample exposed by the oval orifice. |
| Test fluid: | Synthetic menstrual fluid. |
| F) 45° IMPACT CAPACITY | |
| Purpose: | To determine the fluid retention capacity of an absorbent material by measuring its ability to accept and retain a finite discharge of fluid at an inclined plane. |
| Test procedure: | With reference to FIG. 13, the impact capacity on a 2 inch by 10 inch sample is measurd by weighing the amount of fluid that is retained in the sample placed on a 45° inclined plane, on which 25 cubic centimeters of test fluid has been released from an overhanging burette. The burette barely touches the sample at a point approximately 2 inches away from its upper extremity. |
| Test fluid: | Synthetic menstrual fluid. |
| G) FLUID CAPACITY AND COLLAPSE | |
| Purpose: | To determine the fluid saturation capacity of an absorbent material by measuring the maximum amount of fluid the absorbent material can hold under a predetermined pressure. In addition, the degree of collapse (or gain) of the absorbent material upon fluid saturation is determined. |
| Test procedure: | With reference to FIG. 14, the fluid capacity of a pre-weighted 4 inches by 4 inches sample is obtained by measuring the amount of fluid that is required to saturate the sample placed under a 0.05 psi pressure (achieved with a free moving top plexiglass plate). The test fluid is introduced through a small hole having ⅛ of an inch diameter located in the center of the plate. The change in thickness of the sample is measured. The difference in the dry and the wet thickness is recorded and the percentage of gain or collapse derived. |
| Test fluid: | Synthetic menstrual fluid. |
| H) INCLINED PLANE WICKING | |
| Purpose: | To determine the wicking capacity/capillary action of an absorbent material by measuring the amount of fluid uptake and the distance of fluid migration as a function of time at an inclined plane. |
| Test procedure: | With reference to FIG. 15, the wicking capacity of a 2 inches × 10 inches sample is obtained by placing it on a 45° inclined plexiglass plane with the lower end of the sample dipped into a grooved depression which constitutes the liquid bath for the sample. A constant fluid level is maintained by introducing measured amounts of fluid into the bath via a micrometric solenoid valve (activated by an automatic level control deveice). The advancing liquid front moving up the sample is monitored by measuring the distance or height the fluid travels above the bath at specific time intervals, and the amount of fluid uptake is recorded. |
| Test fluid: | 1% NaCl solution. |
| I) WET BACK | |
| Purpose: | To determine the ability of the absorbent material to absorb and retain fluid under a pre-determined pressure while preventing transfer of fluid to another surface. |
| Test procedure: | The wet-back characteristics of a pre-weighted 2 inches × 8 inches sample is obtained by first adding 2 cc/g of synthetic menstrual fluid through an elliptical orifice on the sample under a pressure of 0.04 psi. After the fluid has been absorbed and dispersed in the sample for 3 minutes, 10 plies of 2 inches × 6 inches NuGuaze (Trademark) substrate are placed on the sample and a "cushioned" pressure of 0.25 psi is applied. The quantity of liquid transferred after 3 minutes to the substrate is measured in grams. |
| Test fluid: | Synthetic menstrual fluid. |
| J) LATERAL FLEXIBILITY/STABILITY | |
| Purpose: | To determine the lateral flexibility and structural stability of a thin absorbent sheet by subjecting the sample to side compression. |
| Test procedure: | With reference to FIG. 16, the lateral flexibility/stability of 2¼ inches × 8¼ inches (rounded ends) sample is obtained by placing the sample in between two plexiglass curves (simulating the inner thighs of a wearer); the stationary curve is attached to a compression load cell in an Instron unit and a speed of 500 millimeters per minute (mm/min) is imparted to the moving curve. The sample is securely placed in between the two curves with three metal support rods stemming from the stationary curve and slidingly received in the moving curve. The force required to compress the sample to one inch is recorded. The wet test is done by adding 2 cc/g of fluid to the absorbent material and subjecting it to the lateral compression. |
| Test fluid: | Synthetic menstrual fluid. |

DISCUSSION

For a better understanding of the invention, the test results in Tables 2 and 4 and the graphs of FIGS. 17 and 18 will be discussed. A direct comparison is made between untreated wood pulp fluff and calendered and perf-embossed wood pulp fluff because the latter is intended as a direct replacement for untreated pulp-fluff. The test results in Tables 1 and 3 are not discussed here since they relate to a product in intermediate states of fabrication. This data simply illustrates how the various steps of the calendering and perf-embossing process affect the properties of the fibrous material.

The calendered and perf-embossed wood pulp fluff sheet exhibits a considerable improvement in structural integrity over untreated wood pulp fluff. The dry tensile strength considerably increases from virtually nothing for untreated wood pulp fluff to an average of 1.8 lbs/inch for calendered and perf-embossed wood pulp fluff, which is considered to be satisfactory for practical applications, permitting to obtain an absorbent core highly resistant to mechanical stress capable to retain its shape in use.

Unprocessed wood pulp fluff has better penetration time, 45° impact capacity and absorbent capacity characteristics over calendered and perf-embossed wood pulp fluff. These difference directly result from the denser fibrous network of the calendered and perf-embossed wood pulp fluff, however, they are not significantly to a point where the calendered and perf-embossed wood pulp fluff is no longer capable to efficiently absorb fluid.

A major improvement is observed in wicking power of the fibrous web resulting from the calendering and perf-embossing process. Referring to FIGS. 17 and 18, it appears clearly that unprocessed wood pulp fluff has a very limited ability to wick fluid. Over a period of 10 minutes the fluid front has barely exceeded a distance of 5 centimeters. In the same conditions, calenders and perf-embossed wood pulp fluff exhibits a much superior wicking action, pulling fluid over a distance of approximately 27 centimeters which represents an improvement by a factor in excess of 5.

The improvement in the wicking characteristics of calendered and perf-embossed wood pulp fluff compensates for the reduction in absorbent capacity by comparison to unprocessed wood pulp fluff, by the capability of the calendered and perf-embossed fibrous network to disperse fluid into a layer absorbent volume. This is reflected by the fluid uptake values which are almost the same for the compared wood pulp fluff materials. Undeniably, unprocessed wood pulp fluff has a much better absorbent capacity than calendered and perf-embossed wood pulp fluff and theoretically, the amount of fluid it can absorb is superior to what the calendered and perf-embossed wood pulp fluff can absorb. However, in practice, it is extremely difficult to use the entire absorbent volume of unprocessed wood pulp fluff because fluid tends to remain localized, causing saturation. The calendering and perf-embossing process of wood pulp fluff considerably improves its performance by achieving a certain balance between its various attributes, improving some at the expense of others, but however, achieving an overall gain in efficiency.

Further, the calendered and perf-embossed wood pulp fluff has a better ability to retain the absorbed fluid (i.e. drying power) than unprocessed pulp fluff. Accordingly, calendered and perf-embossed pulp is less likely to wet adjacent surfaces that may come in contact with the absorbent structure than is the case for unprocessed pulp fiber.

EXAMPLE 3

A sanitary napkin comprising an absorbent and flexible calendered perf-embossed cellulosic pulp fluff sheet as its absorbent core.

Figure 11:
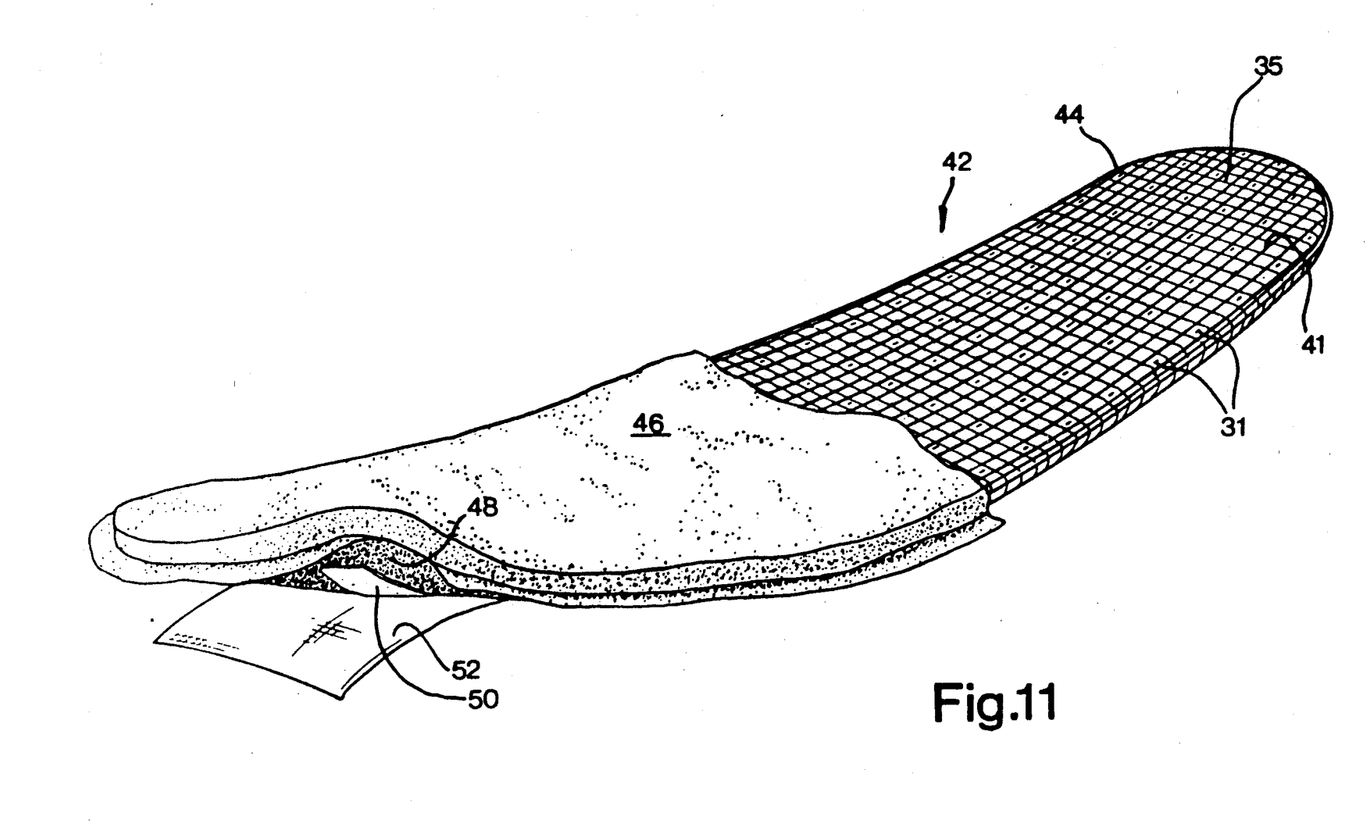
FIG. 11 is a perspective fragmentary view of a sanitary napkin according to the invention, the absorbent core thereof being partially exposed.

Referring to FIG. 11, a sanitary napkin 42 comprises an absorbent core 44 constructed in accordance with Example 1. The core 44 includes throughout its entire surface perforations 31 created at the perforation stage of the perf-embossing treatment, and laterally and longitudinally extending lines 35 and 41, respectively, created at the embossing stages. The width of the absorbent core 44 is of importance to achieve good comfort, good stability and, at the same time, to have satisfactory fluid absorbance characteristics. The narrower the core 44, the higher its comfort potential becomes, however, the risk of failure of the napkin increases because it becomes unstable and its absorbency characteristics are adversely affected by the reduction of the available fluid absorption surface. There is a delicate balance between these factors. It has been found that width in the range of from about 1¾ inches to about 2¼ inches is a satisfactory compromises and most preferably the width is of about 2⅛ inches. The thickness of the absorbent core 44 is of about 0.1 inch measured at 0.05 psi pressure and its length of about 8 inches.

The lateral flexibility of the absorbent core 44 is also important for good comfort. A lateral flexibility in the dry state in the range of about 700 g to 1700 g has been found adequate. The most preferred range is of about 1100 g to 1400 g. A lateral flexibility in the wet state in the range of about 550 g to 950 g is satisfactory.

The remaining structure of the sanitary napkin includes an envelope to confine the absorbent core 44, comprising a fluid permeable side 46 for transferring the menstrual fluid to the absorbent core 44, a fluid impermeable side 48 provided with an adhesive band 50 covered by a peelable backing 52. The adhesive band permits attachment of the sanitary napkin to the user's underpants.

Sanitary napkins in accordance with Example 3 are found in use to possess a better wicking capability as that of napkin having an absorbent core made of unprocessed cellulosic pulp fluff. The sanitary napkin of the invention is found to be objectively somewhat less flexible than peat moss composite absorbent core napkins, but this was not observed as significantly affecting the comfort for wearers in use. It was further found that the sanitary napkins in accordance with the invention are surprisingly more resistant to bunching and deforming than napkins with absorbent cores of unprocessed cellulosic pulp fluff material leading to better overall performance in terms of protection from leakage and retention of product shape.

The scope of the present invention is not limited by the description, examples and suggested uses herein and modifications can be made without departing from the spirit of the invention. For example, additional embossing patterns that provide either aesthetic or functional qualities to the calendered and perf-embossed cellulosic pulp fluff sheets of the invention may be provided. The absorbent cores of the present invention may also be utilized in diverse products including incontinence pads, absorbent cores as inserts for diapers or tampons, or as desiccants for use in packaging materials to keep goods dry during shipping or storage.

Application of the product and methods of the present invention for sanitary and other health care uses can be accomplished by any sanitary protection, incontinence, medical, and absorbent methods and techniques as are presently or prospectively known to those skilled in the art. Thus it is intended that the present invention cover the modifications and variations of this invention provided that they come within the scope of the appended claims and their equivalents.

We claim:

1. A thin and highly absorbent article comprising a densified and perf-embossed cellulosic pulp fluff sheet exhibiting a fiber density profile of alternating high fiber density and low fiber density zones, said high fiber density zones being arranged in an interconnected network so as to be capable to disperse fluid through the high fiber density network and into the cellulosic pulp fluff sheet by capillary action, said interconnecting network forming hinge areas increasing the flexibility of the cellulosic pulp fluff sheet, said perf-embossing forming a plurality of through slits dispersed about said network.

2. A thin and highly absorbent article as defined in claim 1, comprising a calendered cellulosic pulp fluff sheet.

3. A thin and highly absorbent article as defined in claim 1, comprising a calendered and perf-embossed cellulosic pulp fluff sheet.

4. A thin and highly absorbent article as defined in claim 1, wherein said cellulosic pulp fluff sheet has a density in the range of about 0.2 to 0.25 grams per cubic centimeter.

5. A thin and highly absorbent article as defined in claim 1, wherein said cellulosic pulp fluff sheet has an absorbent capacity of least of about 4 cubic centimeters per gram.

6. A thin and highly absorbent article as defined in claim 1, wherein said cellulosic pulp fluff sheet has an absorbent capacity of about 6 cubic centimeters per gram.

7. A thin and highly absorbent article as defined in claim 1, wherein said cellulosic pulp fluff sheet has a dry thickness in the range of about 0.075 to 0.2 inches measured at 0.05 pounds per square inch pressure.

8. A thin and highly absorbent article as defined in claim 1, wherein said cellulosic pulp fluff sheet has a dry thickness in the range of about 0.09 to 0.15 inches measured at 0.05 pounds per square inch pressure.

9. A thin and highly absorbent article as defined in claim 1, wherein said cellulosic pulp fluff sheet has a dry tensile strength at least of about 1 pound per inch in the machine direction.

10. A thin and highly absorbent article as defined in claim 1, wherein said cellulosic pulp fluff sheet has a dry tensile strength at least of about 2 pounds per inch in the machine direction.

11. A thin and highly absorbent article as defined in claim 1, wherein said cellulosic pulp fluff sheet has a density in the range of about 0.1 to 0.3 grams per cubic centimeter.

12. A thin and highly absorbent article as defined in claim 1, wherein said network in which said high density zones are arranged comprises a first group of substantially parallel lines of high density regions and a second group of substantially parallel lines high density regions, said first group of lines being oriented so as to intersect said second group of lines.

13. A thin and highly absorbent article as defined in claim 12, wherein said first and second groups of substantially parallel high density regions intersect at approximately right angles so as to form a grid-like network.

14. A thin and highly absorbent article as defined in claim 12, wherein said first group of substantially parallel high density regions are arranged substantially transversely and said second group of substantially parallel high density regions are arranged substantially longitudinally.

15. A thin and highly absorbent article comprising a densified and perf-embossed cellulosic pulp fluff sheet exhibiting a fiber density profile of alternating high fiber density and low fiber density zones, said high fiber density zones being arranged in an interconnected network so as to be capable to disperse fluid through the high fiber density network and into the cellulosic pulp fluff sheet by capillary action and having a density in the range of about 0.1 to 0.3 gram per cubic centimeter, an absorbent capacity at least of about 4 cubic centimeters per gram and a thickness in the range of about 0.075 to 0.2 inches measured at 0.05 pounds per square inch pressure, said perf-embossing forming a plurality of through slits dispersed about said network 16. A disposable absorbent product selected from the group consisting of sanitary napkins, incontinence products, diapers and wound dressings comprising a densified and perf-embossed cellulosic pulp fluff sheet exhibiting a fiber density profile of alternating high fiber density and low fiber density zones, said high fiber density zones being arranged in an interconnected network so as to be capable of dispersing fluid through the high fiber density network and into said cellulosic pulp fluff sheet by capillary action said interconnecting network forming hinge areas increasing the flexibility of the cellulosic pulp fluff sheet, and wherein said cellulosic pulp fluff sheet has a density in the range of about 0.1 to 0.3 grams per cubic centimeter, and wherein said cellulosic pulp fluff sheet has a dry thickness in the range of about 0.075 to 0.2 inches measured at 0.05 pounds per square inch pressure, said perf-embossing forming a plurality of through slits dispersed about said network.

17. A disposable absorbent product as defined in claim 16, wherein said cellulosic pulp fluff sheet has a dry thickness in the range of about 0.09 to 0.15 inches measured at 0.05 pounds per square inch pressure.

18. A thin, absorbent and flexible sanitary napkin having an improved absorbent layer comprising a calendared and perf-embossed cellulosic pulp fluff sheet which is sufficiently flexible to be worn comfortably by a wearer of the sanitary napkin wherein said cellulosic pulp fluff sheet exhibits a fiber density profile of alternating high fiber density and low fiber density zones, said high fiber density being arranged in an interconnected network so as to disperse fluid through the high fiber density network and into the cellulosic pulp fluff sheet by capillary action and has a density in the range of about 0.1 to 0.3 grams per cubic centimeter, and wherein said absorbent layer has a lateral flexibility in the dry state in the range of about 700 grams to 1700 grams, said perf-embossing forming a plurality of through slits dispersed about said network 19. A sanitary napkin as defined in claim 18, wherein said absorbent layer has a lateral flexibility in the dry state in the range of about 1100 grams to 1400 grams.

20. A sanitary napkin as defined in claim 18, wherein said absorbent layer has a lateral flexibility in the wet state in the range of about 550 grams to 950 grams.

* * * * *